US005641862A

United States Patent [19]
Rutter et al.

[11] Patent Number: 5,641,862
[45] Date of Patent: *Jun. 24, 1997

[54] GENERAL METHOD FOR PRODUCING AND SELECTING PEPTIDES WITH SPECIFIC PROPERTIES

[75] Inventors: William J. Rutter; Daniel V. Santi, both of San Francisco, Calif.

[73] Assignee: The Regents Of The University Of California, Oakland, Calif.

[*] Notice: The term of this patent shall not extend beyond the expiration date of Pat. No. 5,438,119.

[21] Appl. No.: 412,710

[22] Filed: Mar. 29, 1995

Related U.S. Application Data

[63] Continuation of Ser. No. 981,759, Nov. 25, 1992, Pat. No. 5,438,119, which is a continuation of Ser. No. 525,899, May 18, 1990, Pat. No. 5,266,684, which is a division of Ser. No. 189,318, May 2, 1988, Pat. No. 5,010,175.

[51] Int. Cl.$^6$ .............................. A61K 38/02; C07K 5/00; C07K 7/00
[52] U.S. Cl. ................... 530/334; 530/333; 530/300
[58] Field of Search ......................... 530/334, 300, 530/333; 514/2

[56] References Cited

U.S. PATENT DOCUMENTS

| | | | |
|---|---|---|---|
| 4,510,083 | 4/1985 | Blacklock et al. | 260/112.5 |
| 4,572,894 | 2/1986 | Imahori et al. | 435/68 |
| 4,833,092 | 5/1989 | Geysen | 436/501 |
| 4,946,778 | 8/1990 | Ladner et al. | 435/69.6 |
| 5,010,175 | 4/1991 | Rutter et al. | 530/334 |
| 5,053,454 | 10/1991 | Judd | 525/54.11 |
| 5,182,366 | 1/1993 | Huebner et al. | 530/334 |
| 5,194,392 | 3/1993 | Geysen | 436/518 |
| 5,223,409 | 6/1993 | Ladner et al. | 435/69.7 |
| 5,266,684 | 11/1993 | Rutter et al. | 530/334 |
| 5,438,119 | 8/1995 | Rutter et al. | 530/333 |

FOREIGN PATENT DOCUMENTS

| | | |
|---|---|---|
| 0260634 | 3/1988 | European Pat. Off. . |
| 0383620 | 8/1990 | European Pat. Off. . |
| 86-28313 | 6/1985 | United Kingdom . |
| WO86/00991 | 2/1986 | WIPO ........................ 33/53 |
| WO86/06487 | 11/1986 | WIPO ........................ 33/53 |
| WO89/04325 | 5/1989 | WIPO ........................ 7/10 |

OTHER PUBLICATIONS

Berman, J. et al., "Rapid Optimization of Enzyme Substrates Using Defined Substrate Mixtures" *J. of Biol. Chem.* (1992) 267:1434–1437.

Creighton, T.E. *Proteins*, Wett. Freeman & Co., 1984, pp. 39–45.

Flynn et al., "Peptide–binding Specificity of the Molecular Chaperone BiP" *Nature* (1991) 353:726–730.

Furka et al., (1988) 14th Int'l Congress of Biochemistry vol. 5, abstract FR:013.

Furka, A. Sebestyen . . . More Peptides by Less Labor Abstract, 10th Int. Symp. on Med. Chem., Budapest.

Furka, A. et al., "Computer Made Electrophoretin Peptide Maps," 2nd Int. Conf. on Biochem. Symp. Kesythely.

Furka, A. et al., "General Method for Rapid Synthesis of Multicomponent Pep Mix," *Int. J. Pep Res* 37:487–493.

Furka et al., "Cornucopia of Peptides by Synthesis," Publication date unknown.

Getzoff et al. "Mechanisms of Antibody Binding to a Protein" *Science* (1987) 235:1191–1196.

Geysen, H.M. et al., "Use of Peptide Synthesis to Probe Viral Antigens for Epitopes to a Resolution of a Single Amino Acid" *Proc Natl Acad Sci USA* (1984) 81:3998–4002.

Geysen, et al., "Chemistry of Antibody Binding to a Protein" *Science* (1987) 235:1184–1190.

Houghten et al., "Simultaneous Multiple Peptide Synthesis: The Rapid Preparation of Large Numbers of Discrete Peptides for Biological, Immunological, and Methodological Studies" *Biotechniques* (1986) 4(6):522–528.

Houghten, R.A., "General Method for the Rapid solid–Phase Synthesis of Large Numbers of Peptides: Specificity of Antigen–Antibody Interaction at the Level of Individual Amino Acids", *Proc. Natl. Acad. Sci. USA*, (1985), 82:5131–5135.

Houghten et al., "Generation and Use of Synthetic Peptide Combinatorial Libraries for Basic Research and Drug Discovery" *Nature* (1991) 354:84–86.

Kemp et al., "Rate Constants for Peptide ρ–Nitrophenyl Ester Coupling Reactions in Dimethylformamide. A Model for Steric Interactions in the Peptide Bond Forming Transition State" *J. Org. Chem.* (1974) 39(26):3841–3847.

Kovacs, J., "Racemization and Coupling Rates of Nα–Protected Amino Acids and Peptide Active Esters: Predictive Potential" *The Peptides: Analysis, Synthesis, Biology* (1980) Gross et al. (ed.) 485–539.

Lam et al., "A New Type of Synthetic Peptide Library for Identifying Ligand–Binding Activity" *Nature* (1991) 354: 82–84.

Lu, Heieng et al., Chem. Abs. 106(1):2453f, 1986.

(List continued on next page.)

*Primary Examiner*—Avis M. Davenport
*Attorney, Agent, or Firm*—Karl Bozicevic; Fish & Richardson

[57] ABSTRACT

A method to obtain selected individual peptides or families thereof which have a target property and optionally to determine the amino acid sequence of a selected peptide or peptides to permit synthesis in practical quantities is disclosed. In general outline, the method of the invention comprises synthesizing a mixture of randomly or deliberately generated peptides using standard synthesis techniques, but adjusting the individual concentrations of the components of a mixture of sequentially added amino acids according to the coupling constants for each amino acid/amino acid coupling. The subgroup of peptides having the target property can then be selected, and either each peptide isolated and sequenced, or analysis performed on the mixture to permit its composition to be reproduced. Also included in the invention is an efficient method to determine the relevant coupling constants.

22 Claims, 7 Drawing Sheets

OTHER PUBLICATIONS

Merrifield, "Solid Phase Synthesis" *Angewandte Chemie*, (1985) 24(10): 799–810.

Petithory et al., "A Rapid Method for Determination of Endoproteinase Substrate Specificity: Specificity of the 3C Proteinase from Hepatitis A Virus" *Proc. Natl. Acad. Sci. USA* (1991) 88:11510–11514.

Ragnarsson et al., "Studies on the Coupling Step in Solid Phase Peptide Synthesis. Further Competition Experiments and Attempts to Assess Formation of Ion Pairs" *J. Org. Chem.* (1974) 39(26):3837–3841.

Stewart et al., *Solid Phase Peptide Synthesis* (2nd edition), Gross et al, (ed), Pierce Chemical Company (1984).

Zuckermann et al., "Identification of Highest–Affinity Selection from Equimolar Peptide Mixtures Generated by Robotic Synthesis", *Proc. Natl. Acad. Sci. USA* (1992) 89:4505–4509.

| AMINO ACID | Ala | Arg | Asn | Asp | Cys | Gln | Glu | Gly | His | Ile | Leu | Lys | Met | Phe | Pro | Ser | Thr | Trp | Tyr | Val |
|---|---|---|---|---|---|---|---|---|---|---|---|---|---|---|---|---|---|---|---|---|
| ALA | ///// | 0.37 | 0.60 | 0.48 | 0.47 | 0.45 | 0.39 | 0.25 | 0.30 | 0.36 | 0.31 | 0.39 | 0.33 | 0.30 | 0.37 | 0.48 | 0.51 | 0.27 | 0.32 | 0.90 |
| ARG | 0.39 | ///// | 0.35 | 0.29 | 0.27 | 0.27 | 0.23 | 0.11 | 0.12 | 0.15 | 0.23 | 0.19 | 0.20 | 0.31 | 0.31 | 0.28 | 0.28 | 0.10 | 0.12 | 0.40 |
| ASP+ASN | 0.50 | 0.36 | ///// | ///// | 0.43 | 0.44 | 0.35 | 0.18 | 0.30 | 0.36 | 0.38 | 0.37 | 0.24 | 0.36 | 0.39 | 0.46 | 0.38 | 0.22 | 0.39 | 1.27 |
| GLU+GLN | 0.78 | 0.47 | 0.96 | 0.79 | 0.60 | ///// | ///// | 0.18 | 0.37 | 0.45 | 1.07 | 0.54 | 0.35 | 0.43 | 0.54 | 0.65 | 0.56 | 0.34 | 0.44 | 1.80 |
| GLY | 0.39 | 0.33 | 0.76 | 0.51 | 0.46 | 0.53 | 0.36 | ///// | 0.34 | 1.39 | 0.28 | 0.36 | 0.97 | 0.30 | 0.43 | 0.60 | 0.49 | 0.28 | 0.36 | 0.92 |
| HIS | 0.08 | 0.06 | 0.09 | 0.08 | 0.10 | 0.05 | 0.05 | 0.03 | ///// | 0.05 | 0.08 | 0.04 | 0.03 | 0.07 | 0.10 | 0.11 | 0.06 | 0.03 | 0.02 | 0.14 |
| ILE | 0.05 | 0.02 | 0.06 | 0.04 | 0.04 | 0.06 | 0.03 | 0.02 | 0.02 | ///// | 0.03 | 0.03 | 0.03 | 0.02 | 0.05 | 0.06 | 0.04 | 0.01 | 0.01 | 0.00 |
| LEU | 0.31 | 0.19 | 0.32 | 0.28 | 0.34 | 0.31 | 0.20 | 0.14 | 0.21 | 0.21 | ///// | 0.22 | 0.25 | 0.26 | 0.23 | 0.31 | 0.29 | 0.12 | 0.13 | 0.49 |
| LYS | 0.28 | 0.13 | 0.32 | 0.26 | 0.23 | 0.22 | 0.18 | 0.11 | 0.14 | 0.12 | 0.18 | ///// | 0.14 | 0.10 | 0.24 | 0.26 | 0.22 | 0.10 | 0.11 | 0.44 |
| MET | 0.50 | 0.23 | 0.44 | 0.36 | 0.61 | 0.29 | 0.27 | 0.11 | 0.22 | 0.26 | 0.44 | 0.28 | ///// | 0.38 | 0.28 | 0.31 | 0.30 | 0.18 | 0.32 | 1.33 |
| PHE | 0.24 | 0.12 | 0.40 | 0.28 | 0.26 | 0.29 | 0.20 | 0.14 | 0.17 | 0.17 | 0.12 | 0.19 | 0.26 | ///// | 0.26 | 0.33 | 0.30 | 0.11 | 0.12 | 0.27 |
| PRO | 0.36 | 0.22 | 0.38 | 0.46 | 0.32 | 0.25 | 0.24 | 0.12 | 0.20 | 0.24 | 0.22 | 0.26 | 0.23 | 0.24 | ///// | 0.35 | 0.33 | 0.19 | 0.21 | 0.57 |
| SER | 0.24 | 0.15 | 0.32 | 0.24 | 0.08 | 0.23 | 0.19 | 0.11 | 0.16 | 0.17 | 0.22 | 0.21 | 0.16 | 0.15 | 0.21 | ///// | 0.19 | 0.16 | 0.16 | 0.43 |
| THR | 0.15 | 0.14 | 0.12 | 0.10 | 0.08 | 0.10 | 0.07 | 0.05 | 0.14 | 0.07 | 0.13 | 0.12 | 0.11 | 0.07 | 0.11 | 0.13 | ///// | 0.06 | 0.07 | 0.21 |
| TYR | 0.25 | 0.11 | 0.42 | 0.28 | 0.37 | 0.25 | 0.20 | 0.11 | 0.14 | 0.14 | 0.13 | 0.15 | 0.20 | 0.12 | 0.31 | 0.28 | 0.28 | 0.11 | ///// | 0.38 |
| VAL | 0.10 | 0.07 | 0.12 | 0.08 | 0.05 | 0.10 | 0.06 | 0.04 | 0.07 | 0.04 | 0.04 | 0.05 | 0.08 | 0.03 | 0.09 | 0.08 | 0.08 | 0.04 | 0.02 | ///// |

FIG.1

TIME 9.00 TO 35.00 min  SWIVEL 15 deg
WAVELENGTH 210 TO 320nm  TILT 20 deg
RESOLUTION HIGH

TABLE I. HPLC SEPARATION AND ANALYSES OF THE MODEL PENTAPEPTIDE: EXPERIMENT I.

| | 1 | 2-a | 2-b | 3 | 4 | 5 | 6 | 7 | 8 | 9 | 10 | 11 | 12 | 13 | 14 | 15 | 15a | 15b |
|---|---|---|---|---|---|---|---|---|---|---|---|---|---|---|---|---|---|---|
| | | | | | | | | | nmol AA IN EACH PEAK | | | | | | | | | |
| Gly | 0.81 | 1.62 | 1.08 | 0.48 | 0.07 | 0.72 | 0.35 | 0.16 | 0.64 | 0.15 | 0.19 | 0.11 | 0.03 | 0.34 | 0.44 | 1.12 (0.06) | 0.49 | 0.95 |
| Leu | | | | 0.45 | 0.09 | 0.63 | | | | | | | | 0.32 | 0.50 | | | |
| Phe | | | | | | | | | 0.53 | | 0.18 | | 0.03 | | | 1.03 (0.15) | 0.45 | 0.79 |
| Pro | 0.73 | 1.14 | | | | | 0.34 | 0.11 | | 0.13 | | 0.09 | | | | | | |
| Val | | | 1.20 | | | | | | | | | | | | | | | |
| Ala | 0.81 | 1.82 | 1.21 | 0.47 | 0.07 | 0.68 | 0.34 | 0.12 | 0.65 | 0.15 | 0.20 | 0.10 | 0.03 | 0.33 | 0.42 | 1.12 (0.18) | 0.45 | 1.00 |
| Lys | | 1.58 | | 0.34 | | | | | 0.52 | | | | | | | | | |
| Met | | | | | 0.05 | | 0.27 | | | 0.11 | | 0.06 | 0.02 | 0.22 | | 0.58 (0.14) | 0.41 | 0.80 |
| Tyr | | | | | | | | 0.10 | | | | | | | 0.44 | 0.35 (0.1) | | |
| Ser | 0.78 | | 0.6 | | | 0.74 | | | | | 0.216 | | | | | | | |
| Gly | 0.81 | 1.62 | 1.08 | 0.48 | 0.07 | 0.72 | 0.35 | 0.16 | 0.64 | 0.15 | 0.19 | 0.11 | 0.03 | 0.34 | 0.44 | 1.12 (0.20) | 0.49 | 0.95 |

FIG. 6

| | A | B | C | D | E | F | G | H | I | J | K | L | M |
|---|---|---|---|---|---|---|---|---|---|---|---|---|---|
| 1 | | AMINO ACIDS | FROM SEQUENCING: | | | | FROM AMINO ACID ANALYSIS | | | STATISTICS | | | REL RATES(b) |
| 2 | | | PEPTIDE RESIN(a) | | FREE PEPTIDE | | | TOTAL AA/CYCLE | | | | | FROM SEQUENCE |
| 3 | POSITION | | FOUND | ADJUSTED | FOUND | ADJUSTED | FOUND,nmol | CYCLE | ADJUSTED | MEAN | SD | SD/MEAN | OF FREE |
| 4 | 1 | Gly | | | 288 | 1.00 | 5.05 | 2.525 | — | | | | |
| 5 | 2 | Lys | | | 34.9 | 0.19 | 0.61 | | 0.23 | 0.21 | 0.02 | 0.10 | 1.00 |
| 6 | | Met | | | 42 | 0.23 | 0.68 | | 0.26 | 0.24 | 0.02 | 0.07 | 1.23 |
| 7 | | Ser | | | 60.5 | 0.32 | 0.83 | SUM= | 0.31 | 0.32 | 0.01 | 0.02 | 1.87 |
| 8 | | Tyr | | | 49.3 | 0.26 | 0.53 | 2.65 | 0.20 | 0.23 | 0.03 | 0.14 | 1.47 |
| 9 | 3 | Ala | | | 132.1 | 1.00 | 2.45 | 2.45 | — | | | | |
| 10 | | Leu | | | 10.9 | 0.20 | 0.701 | | 0.29 | 0.26 | 0.05 | 0.18 | 2.14 |
| 11 | | Phe | | | 20.9 | 0.32 | 0.85 | | 0.35 | 0.33 | 0.01 | 0.04 | 3.64 |
| 12 | | Pro | | | 25.7 | 0.39 | 0.7 | SUM= | 0.29 | 0.32 | 0.05 | 0.16 | 4.66 |
| 13 | | Val | | | 6.4 | 0.10 | 0.34 | 2.591 | 0.14 | 0.11 | 0.02 | 0.20 | 1.00 |
| 14 | 5 | Gly | | 1.00 | 2.2 | 1.00 | | 2.525 | — | | | | |
| 15 | | Lys | 140 | 0.31 | | | | | | | | | |
| 16 | | Met | 160 | 0.33 | | | | | | | | | |
| 17 | | Ser | 120 | 0.27 | | | | | | | | | |
| 18 | | Tyr | 40 | 0.09 | | | | | | | | | |
| 19 | | Gly | 40 | 1.00 | | | | | | | | | | a) THE PEPTIDE WAS SEQUENCED AFTER COUPLING THE FIRST MIX TO THE Gly-RESIN.
b) USED FREE PEPTIDE SEQUENCING VALUES FOR k CALCULATIONS.

FIG. 7

GENERAL METHOD FOR PRODUCING AND SELECTING PEPTIDES WITH SPECIFIC PROPERTIES

CROSS REFERENCES

This application is a continuation of an earlier filed U.S. application Ser. No. 07/981,759 filed Nov. 25, 1992, U.S. Pat. No. 5,438,119, which application is a continuation of an earlier filed U.S. application Ser. No. 07/525,899 filed May 18, 1990, which issued as U.S. Pat. No. 5,266,684, which application is a divisional of U.S. application Ser. No. 07/189,318 filed May 2, 1988, which issued as U.S. Pat. No. 5,010,175 on Apr. 23, 1991, which applications are incorporated herein by reference in their entirety and to which applications we claim priority under 35 USC §120.

TECHNICAL FIELD

The invention relates to synthesis identification, and analysis methods to obtain desired peptide sequences. More particularly, it concerns a method to obtain defined peptide mixtures, to select those which have high affinities for receptor (or other desired property) and to identify and analyze desired members of these mixtures.

BACKGROUND ART

It is now almost a matter of routine to synthesize a single defined peptide sequence using the Merrifield method to "grow" peptide chains attached to solid supports. The process of synthesizing these individual peptides has, in fact, been automated, and commercially available equipment can be used to synthesize routinely peptides of twenty or more amino acids in length. To obtain peptides of arbitrary length, the resulting peptides can further be ligated with each other by using appropriate protective groups on the side chains and by employing techniques permitting the removal of the synthesized peptides from the solid supports without deprotecting them. Thus, the synthesis of individual peptides of arbitrary length is known in the art.

However routine the synthesis of individual peptides may be, it is necessarily laborious. Therefore, in the many cases where it is not previously known which of a multiplicity of peptides is, in fact, the preparation desired, while theoretically it is possible to synthesize all possible candidates and test them with whatever assay is relevant (immunoreactivity with a specific antibody, interaction with a specific receptor, particular biological activity, etc.), to do so using the foregoing method would be comparable to the generation of the proverbial Shakespeare play by the infinite number of monkeys with their infinite number of typewriters. In general, the search for suitable peptides for a particular purpose has been conducted only in cases where there is some prior knowledge of the most probable successful sequence. Therefore, methods to systematize the synthesis of a multiplicity of peptides for testing in assay systems would have great benefits in efficiency and economy, and permit extrapolation to cases where nothing is known about the desired sequence.

Two such methods have so far been disclosed. One of them, that of Houghten, R. A., *Proc Natl Acad Sci USA* (1985) 82:5131–5135, is a modification of the above Merrifield method using individual polyethylene bags. In the general Merrifield method, the C-terminal amino acid of the desired peptide is attached to a solid support, and the peptide chain is formed by sequentially adding amino acid residues, thus extending the chain to the N-terminus. The additions are carried out in sequential steps involving deprotection, attachment of the next amino acid residue in protected form, deprotection of the peptide, attachment of the next protected residue, and so forth.

In the Houghten method, individual polyethylene bags containing C-terminal amino acids bound to solid support can be mixed and matched through the sequential attachment procedures so that, for example, twenty bags containing different C-terminal residues attached to the support can be simultaneously reprotected and treated with the same protected amino acid residue to be next attached, and then recovered and treated uniformly or differently, as desired. The resultant of this is a series of polyethylene bags each containing a different peptide sequence. These sequences can then be recovered and individually biologically tested.

An alternative method has been devised by Geysen, H. M., et al, *Proc Natl Acad Sci USA* (1984) 81:3998–4002. See also WO86/06487 and WO86/00991. This method is a modification of the Merrifield system wherein the C-terminal amino acid residues are bound to solid supports in the form of polyethylene pins and the pins treated individually or collectively in sequence to attach the remaining amino acid residues. Without removing the peptides from support, these peptides can then efficiently be effectively individually assessed for the desired activity, in the case of the Geysen work, interaction with a given antibody. The Geysen procedure results in considerable gains in efficiency of both the synthesis and testing procedures, while nevertheless producing individual different peptides. It is workable, however, only in instances where the assay can be practically conducted on the pin-type supports used. If solution assay methods are required, the Geysen approach would be impractical.

Thus, there remains a need for an efficient method to synthesize a multiplicity of peptides and to select and analyze these peptides for those which have a particular desired biological property. The present invention offers such an alternative by utilizing synthesis of mixtures as well as providing a means to isolate and analyze those members or families of members of the mixture which have the desired property.

DISCLOSURE OF THE INVENTION

By adjustment of the appropriate parameters, the invention permits, for the first time, a practical synthesis of a mixture of a multitude of peptide sequences, in predictable or defined amounts within acceptable variation, for the intended purpose. In addition, the invention permits this mixture to be selected for the desired peptide members, individually or as groups and the determination of sequences of these selected peptides so that they can be synthesized in large amounts if desired. Because mixtures of many peptides are used, prejudicial assumptions about the nature of the sequences required for the target biological activity is circumvented.

Thus, in one aspect, the invention is directed to a method to synthesize a mixture of peptides of defined composition. The relative amount of each peptide in the mixture is controlled by modifying the general Merrifield approach using mixtures of activated amino acids at each sequential attachment step, and, if desired, mixtures of starting resins with C-terminal amino acids or peptides conjugated to them. The compositions of these mixtures are controlled according to the desired defined composition to be obtained by adjustment of individual activated amino acid concentrations according to the rate constants determined for coupling in the particular ligation reactions involved. The invention also provides, and is directed to, a method to determine efficiently the required rate constants appropriate to the specific conditions under which the reaction will be conducted.

It should be noted that while the invention method of synthesis is most usually and practically conducted using solid-supported peptides, there is no reason it cannot be employed for solution phase synthesis, wherein the acceptor amino acid or peptide is simply blocked at the carboxyl terminus.

In another aspect, the invention is directed to a method to select those components (individually or as families) of the mixture which have the desired "target" activity. Sequence information on these peptides can also be obtained. Thus, the invention is also directed to a method to separate the desired peptide, or peptide family, from the original composition; this comprises effecting differential behavior under conditions which result in physical separation of components, such as binding to a selective moiety, differential behavior with respect to solubility, shape or transport, or modification of the structure of selected peptides or mixtures by a reagent or enzyme which converts only the desired peptides to a form that can be conveniently analyzed or separated.

Finally, the invention is directed to the combination of the foregoing with methods to analyze peptide sequences, often while these sequences are still present in mixtures.

In addition to the foregoing aspects, various additional combinations thereof are useful.

BRIEF DESCRIPTION OF THE DRAWINGS

FIG. 1 is a table showing the results of analysis of dipeptides formed using mixtures of activated amino acids with various acceptors.

FIG. 6 is a table showing the results of HPLC separation of a model pentapeptide mixture.

FIG. 7 is a table showing the results of sequencing performed on a pentapeptide mixture.

MODES OF CARRYING OUT THE INVENTION

Figure 2:
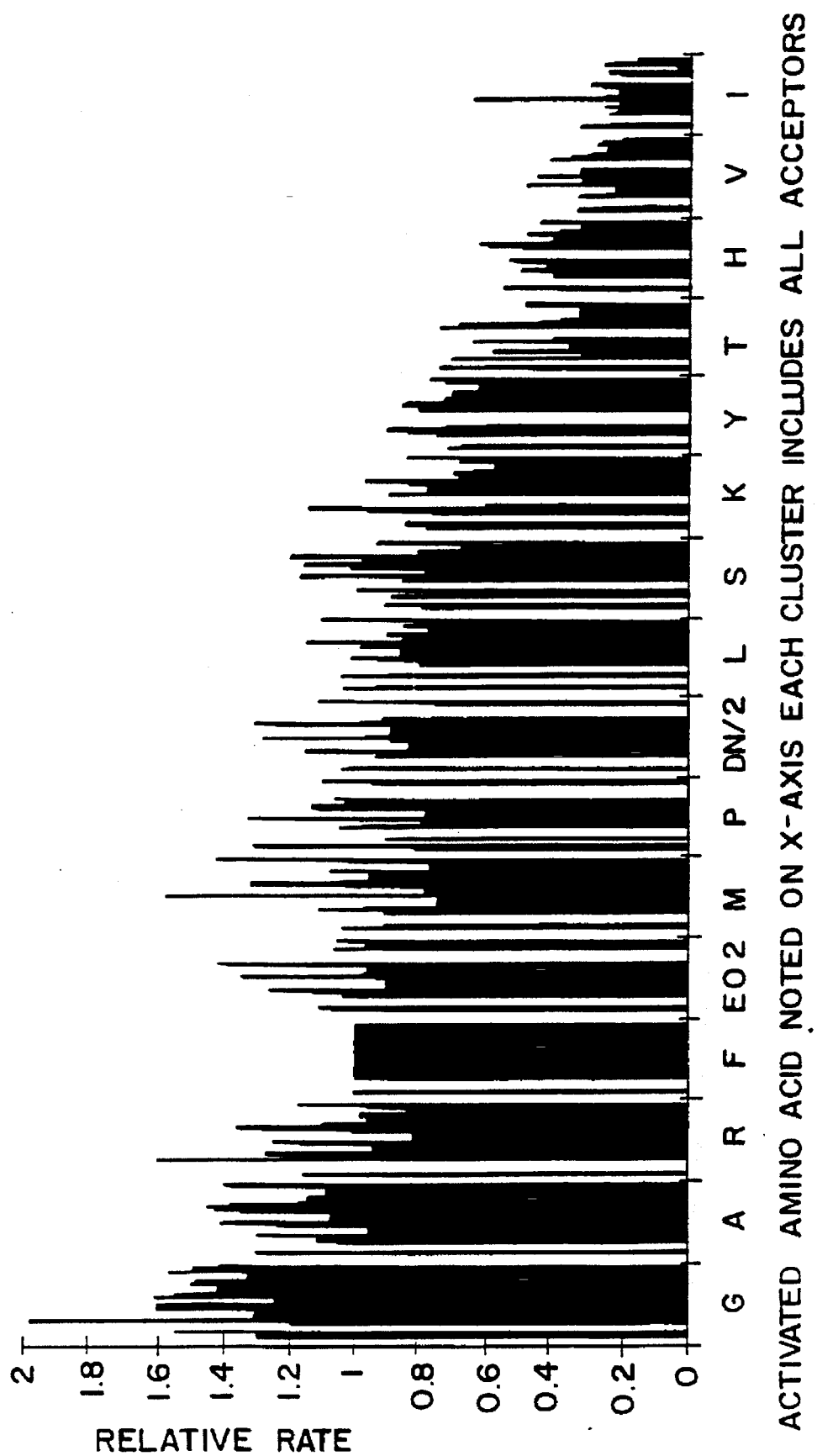
FIG. 2 is a graphical representation of relative rates of conjugation of activated amino acids to solid support-linked peptides with various N-terminal amino acids as tabulated in FIG. 1.

In general, the goal of the invention is to provide a means to obtain and identify one or a family of specific peptide sequences which have a target utility such as ability to bind a specific receptor or enzyme, immunoreactivity with a particular antibody, and so forth. To achieve this end, the method of the invention involves one or more of the three following steps:

1. Preparation of a mixture of many peptides putatively containing the desired sequences;
2. Retrieval or selection from the mixture of the subpopulation which has the desired characteristics; and
3. Analysis of the selected subpopulation to determine amino acid sequence so that the desired peptide(s) can be synthesized alone and in quantity.

Of course, repeated iterations of the three steps using smaller and smaller populations can also be conducted.

Since a complex mixture of peptides is to be synthesized as the starting material for selection, no preconceived ideas of what the nature of the peptide sequence might be is required. This is not to imply that the method is inapplicable when preliminary assumptions can reasonably be made. In fact, the ability to make valid assumptions about the nature of the desired sequence makes the conduct of the method easier.

Using for illustration only the twenty amino acids encoded by genes, a mixture in which each position of the peptide is independently one of these amino acids will contain 400 members if the peptide is a dipeptide; 8,000 members if it is a tripepride; 160,000, if it is a tetrapeptide; 3,200,000 if there are five amino acids in the sequence; and 64,000,000 if there are six. Since alternative forms can be included, such as D amino acids, and noncoded amino acids, the number of possibilities is, in fact, dramatically greater. The mixtures, in order to be subjected to procedures for selection and analysis of the desired members, must provide enough of each member to permit this selection and analysis. Using the current requirement, imposed by limitations of available selection and analysis techniques, of about 100 picomoles of a peptide in order to select it and analyze its structure, the total amount of protein mixture required can be calculated, assuming that the peptides are present in equal amounts. The results of this calculation for peptides containing amino acids selected only from those encoded by the gene are shown in Table 1 below.

It is essential that the synthesis of the mixture be controlled so the component peptides are present in approximately equal, or at least predictable, amounts. If this is achieved, then quantitation of the peptides selected by a protein receptor, or other method, will reflect the dissociation constants of the protein-peptide complexes. If the components of the mixture differ greatly, the amount of selected peptide will also reflect the concentration of that peptide in the mixture. Since it will not be feasible to quantitate the individual amounts of the components of very large mixtures of peptides, it is imperative that the synthesis is predictably controlled.

TABLE 1

| n | Number of Peptides | Mass of mixture |
|---|---|---|
| 2 | 400 | 0.0022 mg |
| 3 | 8,000 | 0.44 mg |
| 4 | 160,000 | 8.8 mg |
| 5 | 3,200,000 | 176 mg |
| 6 | 64,000,000 | 3.5 g |

As shown in the table, even for a peptide of 6 amino acids wherein the mixture contains 64,000,000 separate components, only about 3.5 g of total mixture is required. Since most epitopes for immunoreactivity are often no greater than this length, and receptor binding sites are regions of peptides which may be of similar length, it would be feasible, even at current levels of sensitivity in selection and analysis, to provide a complete random mixture of candidate peptides, without presupposition or "second guessing" the desired sequence. This is further aided if peptides with staggered regions of variable residues and residues common to all components of the mixture can be used, as outlined below.

While the most frequent application of the invention is to discern an individual or small subgroup of amino acid sequences having a desired activity, in some instances it may be desirable simply to provide the mixture per se. Instances in which this type of mixture is useful include those wherein several peptides may have a cooperative effect, and in the construction of affinity columns for purification of several components. The method may also be used to provide a mixture of a limited number of peptides, which can then be separated into the individual components, offering a method of synthesis of large numbers of individual peptides which is more efficient than that provided by individual synthesis of these peptides.

As used herein, the "acceptor" is the N-terminal amino acid of a solid-supported growing peptide or of the peptide or amino acid in solution which is protected at the C-terminus; the "activated" amino acid is the residue to be added at this N-terminus. "Activated" is applied to the status of the carboxyl group of this amino acid as compared to its amino group. The "activated" amino acid is supplied under conditions wherein the carboxyl but not the amino group is available for peptide bond formation. For example, the carboxyl need not be derivatized if the amino group is blocked.

"Target" characteristic or property refers to that desired to be exhibited by the peptide or family, such as specific binding characteristics, contractile activity, behavior as a substrate, activity as a gene regulator, etc.

A. Synthesis of Mixtures of Defined Composition

Two general approaches to the synthesis of defined mixtures are disclosed. The first approach results in a completely arbitrary mixture of all possible peptides containing "n" amino acid residues in approximately equal or predictable amounts, and requires for success the determination of all of the relative rate constants for couplings involved in constructing the desired peptides in the mixture. The second approach takes advantage of certain approximations, but requires that compromises be made with regard to the sequences obtained.

The discussion below in regard to both approaches will concern itself with synthesis of peptides containing residues of the twenty amino acids encoded by the genetic code. This is for convenience in discussion, and the invention is not thus limited. Alternate amino acid residues, such as hydroxyproline, α-aminoisobutyric acid, sarcosine, citrulline, cysteic acid, t-butylglycine, t-butylalanine, phenylglycine, cyclohexylalanine, β-alanine, 4-aminobutyric acid, and so forth can also be included in the peptide sequence in a completely analogous way. The D forms of the encoded amino acids and of alternate amino acids can, of course, also be employed. The manner of determining relative rate constants, of conducting syntheses, and of conducting selection and analysis is entirely analogous to that described below for the naturally occurring amino acids. Accordingly, the results in terms of the number of rate constants required, the number of representative peptides in the mixture, etc., are also directly applicable to peptides which include as one, or more, or all residues, these nonencoded amino acids.

As a general proposition, it is not so simple to obtain mixtures of peptides having a defined composition, as might be supposed. Using the general Merrifield approach, one might assume that a mixture of twenty different derivatized resins, each derivatized with a different amino acid encoded by the gene, might be simultaneously reacted with a mixture containing the N-blocked, activated esters of the twenty amino acids. The random reaction of the activated amino acids with the derivatized resins would then, presumably, result in the 400 possible dipeptide combinations.

But this would only be the result if the rate of all 400 possible couplings were the same. A moment's reflection will serve to indicate that this is not likely to be the case. The rate of coupling of the suitably N-blocked activated carboxyl form of alanine with a resin derivatized with alanine is, indeed, not the same as the rate of reaction of N-blocked carboxy-activated proline with a resin derivatized with alanine, which is, in turn, not the same as the rate of reaction of the N-blocked carboxy-activated proline with a resin derivatized with proline. Each of the 400 possible amino acid couplings will have its own characteristic rate constant. In order to prevent the mixture from containing an undue preponderance of the dipeptides formed in reactions having the faster rate constants, adjustments must be made. The problem will be aggravated upon the attempt to extend the peptide chain with the third mixture of twenty amino acids, and further complicated by extension with the fourth, etc. As more amino acids are added to the chain, the preference for the higher coupling constants is continuously tilted in favor of the faster reacting species to the near exclusion of the peptides which would result from the slower coupling constants.

According to the method of the invention, the differential in coupling constants is compensated by adjustment of the concentrations of the reactants. Reactants which participate in reactions having coupling constants which are relatively slow are provided in higher concentration than those which participate in reactions having coupling constants which are fast. The relative amounts can be precisely calculated based on the known or determined relative rate constants for the individual couplings so that, for example, an equimolar mixture of the peptides results, or so that a mixture having an unequal, but defined concentration of the various peptides results.

The method is similarly applied to solution phase synthesis, wherein the acceptor peptides or amino acids are supplied as a mixture for reaction with an appropriate mixture of activated amino acids. Either or both mixtures are concentration-adjusted to account for rate constant differentials.

A.1 Determination of Coupling Constants

In order to adjust the relative concentrations of reactants, it is, of course, necessary to know the relative rate constants on the basis of which adjustment will be made. The invention method offers a direct means to obtain sufficiently precise values for these relative rate constants, specifically in the context of the reaction conditions that will be used for the peptide mixture synthesis.

Alternative methods available in the art for estimating the 400 rate constants needed for synthesis of peptides utilizing all twenty "natural" amino acids are based on hypothesis and extrapolation. For example, Kemp, D. S. et al, *J Org Chem* (1974) 39:3841–3843, suggested a calculation based on the coupling to glycine of the nineteen remaining amino acids and of glycine to the remaining nineteen, and then relating these to the constant for Gly-Gly coupling. This method, indeed, predicted that certain couplings would have aberrant rate constants, in particular those wherein the N-unblocked acceptor amino acid was a prolyl residue.

In addition, Kovacs, J., in "The Peptides: Analysis, Synthesis, Biology" (1980), Gross, et al, ed, pp 485–539 provided a method to extrapolate rate constants for studied couplings to those not studied based on the nature of the side chains, solvents and other conditions. These predicted values in general agreed with those of Kemp.

The method of the present invention, however, provides for a precise determination of any desired coupling constant relative to the others under the specific conditions intended to be used in the synthesis. It is applicable not only to the twenty "natural" amino acids studied by others, but to D-forms and non-coded amino acids as well. The method employs, for example, the polypropylene-bagged resins of Houghten, R. (supra). Each of the twenty amino acyl resins is packaged in a polypropylene bag, and the twenty packets are placed in one container having excess amounts of all twenty activated amino acids. Reaction is allowed to proceed for a set period sufficient to complete coupling to the acceptor amino acids linked to resin. Each of the bags is then subjected to treatment to release the dipeptides, resulting in twenty mixtures of twenty dipeptides each, each mixture being analyzed separately, using standard techniques of amino acid analysis. The relative amounts of the N-terminal amino acids for the mixture of each particular bag represents the relative values of the coupling constants of each of these amino acids for the same C-terminal residue. The relative amount of coupling between various bags gives the comparative activities of the residues as acceptors. Thus analysis of all twenty bags thus results in relative values for the 400 desired constants. The couplings can be conducted in a manner and under conditions precisely the same as those expected to be used for the synthesis; the nature of activating, blocking, and protecting groups can also be standardized.

(If absolute rate constants are desired, absolute values can be determined for a given activated amino acid with respect to each acceptor and the remainder calculated from the appropriate ratios.)

A.2 Adjustment of Concentrations

The relative rate constants determined as described above can then be used in adjusting the concentrations of components in synthesizing the desired mixture of defined concentration. In principle, the concentrations of the components which are slowly reactive are increased, and the expected resulting concentration of products is calculated. In order to obtain a mixture of equimolar concentration, the various rate constants must be accounted for in an algorithm which is not straightforward to calculate, since the effect of concentration of the activated participant in the coupling will be different depending on the acceptor component, and conversely. Computer-based simulations involving all parameters can be designed.

In practice, a mixture of acceptors on a resin with similar relative reactivities is reacted with the appropriate mixture of known concentrations of activated amino acids. The identity and quantity of products are determined from known values (amount of reactants used, and amounts of products formed), the relative rate constants for each of the couplings are calculated. Knowing the relative rate constants and the relative amounts of products desired, the amounts of reactants can be adjusted to achieve this goal. Currently, the computations are performed by the Euler or second-order Runge-Kutta methods (see Press, W. et al, "Numerical Recipes" (1986) Cambridge University Press, New York, chapter 15).

However, this is usually not needed. Under ordinary application of the method, the acceptor concentration is held constant for all acceptors of similar reactivity, and only the activated residue concentration is varied inversely as to its relative rate of coupling. Acceptors which differ in their capacity to couple are used in separate reaction mixtures, as outlined below.

The remainder of the synthesis method employs known procedures. A coupling protocol is designed wherein the initial mixture of all derivatized resins is similarly reactive compared to the others with the activated, protected next amino acid residue or mixture. After this initial coupling, unreacted amino groups can, if needed, be capped, for example with acetyl groups, by reacting with acetic anhydride, the reacted amino acyl residues are deblocked, and next N-blocked, C-activated amino acid residue mixture added. After this addition step, the unreacted amino groups can, if desired, again be capped, and the reacted residues deprotected and treated with the subsequent N-blocked, C-activated amino acid.

Isolation of full-length peptides can be further aided by utilizing a final amino acyl residue which is blocked with a selectable group such as tBOC-biotin. When the side chains are deprotected and peptide released from the resin, only full-length peptides will have biotin at the amino terminus, which facilitates their separation from the capped peptides. The biotinylated peptides (which are all full length due to the intermediate capping of incomplete peptides) are conveniently separated from the capped peptides by avidin affinity chromatography. Other specific selectable groups can be used in connection with the protecting group on the final amino acid residue to aid in separation, such as, for example, FMOC, which can also be removed.

In the above-described approach, in order to vary the ratios only of activated residues in a particular mixture, it has been assumed that all acceptors have the same relative rates with all activated amino acids. If they do not [for example Pro has been reported to differ in relative rate from other acceptors (Kemp, D. S. et al, *J Org Chem* (1974) 39:3841–3843 (supra))], the simple approach thus far described will be compromised since one cannot conveniently adjust the relative concentrations of the acceptors once coupled to the solid phase. This can be resolved if the acceptors are first separated into groups which have similar relative rates of reactivities. It may also be advantageous for technical reasons, in some cases, to separate acceptors into groups based on their relative rates of reaction, for example, the separation of the very "fast" from the very "slow" reacting acceptors. The ensuing description utilizes "slow" and "fast" to differentiate acceptors which differ in relative rates of coupling with activated amino acids.

In this method, the reaction rates can be normalized to some extent by conducting "slow" and "fast" reactions separately and then sorting into alternate sets to reverse the reactivity rates. This general approach is illustrated as follows.

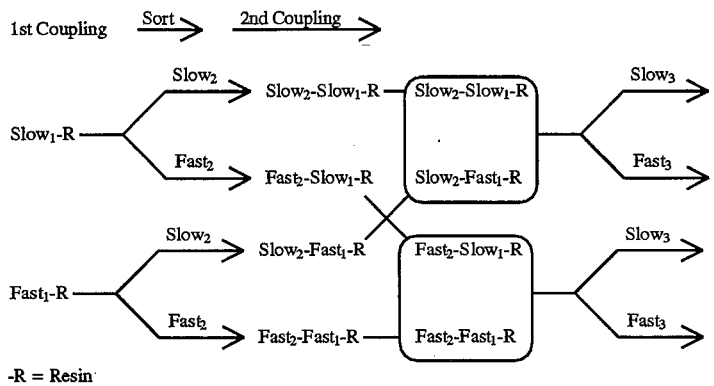

-R = Resin

As shown above, resins bearing amino acid residues which "slowly" conjugate as acceptors for additional residues are reacted separately from those bearing acceptors which have "fast" relative coupling constants. Depending on the particular amino acid from the mixture which subsequently couples, the growing chain will bear, as the N-terminus, an acceptor which is either a "slow" or "fast" reactor. As in every step, slow- and fast-reacting acceptors are conjugated in separate reactions; thus the resins bound to dipeptides N-terminated in slow- and fast-coupled receptors are segregated; each step involves four mixtures as shown. The resins bearing peptides N-terminated in fast couplers are again reacted separately from those N-terminated with slow couplers also segregating the activated residues according to whether they will be slow or fast acceptors when added to the peptide in the second coupling reaction. The sorting is repeated after this reaction, and the fast couplers again segregated from their slower counterparts to continue the synthesis. In instances where the rate of coupling is determined predominately by the coupling constant typical of the acceptor, this "mix-and-match" technique permits ready construction of an approximately equimolar mixture without adjusting the ratios of acceptor in the reaction mixtures.

A.3 Modified Synthesis of Mixtures

In addition to achieving the synthesis of mixtures of random configuration or any particular desired composition by regulating the relative amounts of each sequential residue to be added, a modified approach can be used to obtain particular desired mixtures by introducing acceptable limitations into the sequences of resulting peptides.

For example, positions occupied by each of the twenty candidate amino acids obtained by using mixtures of N-blocked, C-activated amino acid residues in a synthesis step are alternated with positions having the same residue common to all of the peptides in the mixture. In this way, manipulation of concentrations to account for only twenty different rate constants is required in adding the mixture, while the addition of the subsequent common residue can be effected by running the reaction to completion. For example, mixtures of the peptides of the sequence (N to C) $AA_1$-Ala-$AA_3$-Pro-$AA_5$-Gly could be synthesized by using Gly-derivatized resin in the presence of a mixture of blocked, activated amino acids whose concentration ratios are adjusted in inverse proportion to their rate constants for coupling to glycine. (The reaction product can be capped, for example, with acetic anhydride, and then the protected amino groups deblocked for subsequent reaction with an excess of N-blocked, activated proline.) When this addition reaction has gone to completion, the resin is again capped, the protected amino groups deblocked, and a mixture of blocked, activated amino acids inversely proportional in their concentration to their coupling constants with proline residues is added. Subsequent cycles employ an excess of alanine and the appropriate mixture of amino acid residues based on their relative coupling constants to the alanine.

Although the foregoing method places some constraints on the complexity of the resulting mixture, it is, of course, possible to obtain as many members of the mixture as previously, and the algorithms for computing the appropriate mixtures are greatly simplified.

B. Selection

Since the method of the invention results in a complex mixture of peptides, only a few of which are those desired for the target reactivity, it is necessary to select from the mixture those successful products which have the required properties. The nature of the selection process depends, of course, on the nature of the product for which selection is to be had. In a common instance, wherein the desired property is the ability to bind a protein such as an immunoglobulin, receptor, receptor-binding ligand, antigen or enzyme, selection can be conducted simply by exposing the mixture to the substance to which binding is desired. The desired peptides will bind preferentially. (Other, non-protein substances, such as carbohydrates or nucleic acids could also be used.) The bound substances are then separated from the remainder of the mixture (for example, by using the binding substance conjugated to a solid support and separating using chromatographic techniques or by filtration or centrifugation, or separating bound and unbound peptides on the basis of size using gel filtration). The bound peptides can then be removed by denaturation of the complex, or by competition with the naturally occurring substrate which normally binds to the receptor or antibody.

This general method is also applicable to proteins responsible for gene regulation as these peptides bind specifically to certain DNA sequences.

In the alternative, peptides which are substrates for enzymes such as proteases can be separated from the remainder of the peptides on the basis of the size of cleavage products, or substrates for enzymes which add a selectable component can be separated accordingly.

Other properties upon which separation can be based include selective membrane transport, size separation based on differential behavior due to 3-dimensional conformation (folding) and differences in other physical properties such as solubility or freezing point.

Since a number of the members of the mixture are expected to possess the desired target property to a greater or lesser degree, it may be necessary to separate further the components of the smaller mixture which has been selected by standard differentiating chromatographic techniques such as HPLC. On the other hand, it may be desirable to use the subgroup without further separation as a "family" to provide the desired activity. However, in any case, if very large subpopulations are obtained, reapplication of the selection technique at higher stringency may be needed. Analysis, as set forth below, can be conducted on individual components, or on mixtures having limited numbers of components.

Thus, for example, if a mixture of peptides binding to antibody or receptor contains fifty or so members, the salt concentration or pH can be adjusted to dissociate all but the most tightly binding members, or the natural substrate can be used to provide competition. This refinement will result in the recovery of a mixture with a more manageable number of components. A variety of protocols will be evident to differentiate among peptides with varying levels of the target characteristics.

C. Analysis

When individual peptides or manageable mixtures have been obtained, standard methods of analysis can be used to obtain the sequence information needed to specify the particular peptide recovered. These methods include determination of amino acid composition, including the use of highly sensitive and automated methods such as fast atom bombardment mass spectrometry (FABMS) which provides the very precise molecular weight of the peptide components of the mixture and thus permits the determination of precise amino acid composition. Additional sequence information may be necessary to specify the precise sequence of the protein, however. In any event, current technology for sequence analysis permits determination on about 100 picomoles of peptide or less. A variety of analytical techniques are known in the art, and useful in the invention, as described below:

It should be emphasized that certain of these methods can be applied directly to mixtures having limited numbers of components, and the sequence of each component deduced. This application is made without prior separation of the individual components.

The ultimate success of the method in most cases depends on sequence analysis and, in some cases, quantitation of the individual peptides in the selected mixture. Techniques which are current state-of-art methodologies can be applied individually on pure components but also may be used in combination as screens. A combination of diode array detection Liquid Chromatography (DAD-LC), mixture peptide sequencing, mass spectrometry and amino acid analysis is used. To Applicants' knowledge, these standard methods are used for the first time in combination directly on the peptide mixtures to aid in the analysis. The following paragraphs briefly describe these techniques.

HPLC with single wavelength detection provides a rapid estimation of the complexity of mixture and gives a very approximate estimation of amounts of components. This information is contained within the more precise information obtained in DAD-LC.

DAD-LC provides complete, multiple spectra for each HPLC peak, which, by comparison, can provide indication of peak purity. These data can also assign presence of Tyr, Trp, Phe, and possibly others (His, Met, Cys) and can quantitate these amino acids by 2nd derivative or multicomponent analysis. By a post-column derivatization, DAD-LC can also identify and quantitate Cys, His and Arg in individual peptides. Thus, it is possible to analyze for 6 of the 20 amino acids of each separated peptide in a single LC run, and information can be obtained about presence or absence of these amino acids in a given peptide in a single step. This is assisted by knowing the number of residues in each peptide, as is the case in application to the present invention. Also, by correction at 205 nm absorbance for side-chain chromophores, this technique can give much better estimation of relative amounts of each peptide.

Mass spectrometry identifies molecules according to mass and can identify peptides with unique composition, but does not distinguish isomeric sequences. In effect, this method provides similar results as the amino acid analysis (AAA) of isolated peptides; the advantage is that it can be performed on mixtures in a single experiment. The disadvantage is that as applied to mixtures it does not tell which peptide belongs to which LC peak nor provide quantitation; further, some peptides may go undetected. For the present purpose, it is useful in conjunction with one of the other methods.

Mixture peptide sequencing is most useful for identification, especially if the selected peptides are limited in number. As sequence cycles are performed through positions where multiple amino acids were placed, the peptides show multiple derivatized amino acids present in proportion to their amount in the selected peptide. In many cases quantitation of the amino acids in the different cycles will resolve this potential problem; if amino acids are present in the same sequence, they should appear in identical amounts as in the sequencing cycles. Thus, the problem is significant when two or more selected peptides are present in similar amounts. In this case they may be readily distinguishable by combined use of other methods mentioned. As a final resort, group separations or reactions may be performed so that sequencing will provide a unique solution.

HPLC separation and amino acid analysis or sequencing of components could also be performed. Amino acid analysis provides composition, but not sequence. Likewise, the isolated peptides can be sequenced to give the exact solutions of identity. Isolation is more tedious than analysis of mixes, and not doable for very large mixtures; these methods however, are quite practical for a limited number of peptides.

D. Summary

The foregoing approach of preparation of complex mixtures, selection of those members having successful properties, and, if desired, analysis of the chosen few so as to permit large-scale synthesis of the desired peptides permits selection of one or more peptides of a mixture which are superior in their properties in binding to various moieties including proteins, such as enzymes, receptors, receptor-binding ligands or antibodies, nucleic acids, and carbohydrates, reaction with enzymes to form distinct products, or other properties such as transport through membranes, anti-freeze properties, and as vaccines. In general, although short-cut methods which presuppose some features of the sequence are also available, the method, in principle, offers the opportunity to maximize the desired property without preconceived ideas as to the most successful sequence.

EXAMPLES

The following examples are intended to illustrate but not to limit the invention.

Example 1

Determination of Coupling Constants

Individual resins in polypropylene bags derivatized to each of the 20 DNA-encoded amino acids were prepared and collectively reacted with an equimolar mixture of BOC-protected amino acids in the presence of the coupling reactant diisopropylcarbodiimide (DIPCDI). The 20 bags, each containing a mixture of resulting dipeptides, were individually treated to decouple the dipeptides from the resins and the amino acid composition of each mixture was determined. The results, discussed below, produced relative values of rate constants for most of the 400 possible couplings.

In more detail, the synthesis was performed using a modified method of that disclosed by Houghten, R. A. (*Proc Natl Acad Sci USA* (1985) 32:5132–5135).

Twenty labeled polypropylene bags (75 u; 1 in.×1 in.; McMaster-Carr, Los Angeles, Calif.) each containing ~100 mg of p-methyl-BHA-resin hydrochloride (¯0.75 mmol/g; d150–200 mesh; ABI) were gathered in a 250 ml polyethylene wide-mouth screw-cap vessel, washed with 2×100 ml of DCM, and neutralized with 3×100 ml of 5:95 (V/V) DIEA in DCM and washed with 2×100 ml DCM.

Each bag was labeled with black India ink for identification and placed in separate vessels (125 ml screw cap, Nalgene). To each was added 0.8 mmol (10-fold excess) of an amino acid dissolved in 2 ml DCM (A,D,C,E,G,I,K, M,F,P,S,T,Y,V), 0.2 ml DMF and 1.8 ml DCM (R,H,L,W), or 2 ml DMF(Q,N), 2 ml of 0.4 mol DIPCDI in DCM (0.8 mmol) was added to each and 0.8 mmol HOBT was added to the reactions containing Q and N. The coupling time was one 1 hour at room temperature with mechanical shaking. The bags were combined in a 250 ml vessel, washed with 100 ml DMF and then 100 ml DCM. The BOC protecting group was removed by treatment with 100 ml 55% trifluoroacetic acid in DCM for 30 min. on a shaker.

The gathered bags were washed with 1×100 ml DMF, 2×100 ml of 5% DIEA in DCM and washed with 2×100 ml DCM. The following mixture was added to the collection of bags: all 20 BOC amino acids (0.8 mmol each), 4.8 ml DMF, and 35.2 ml DCM; 40 ml of a 0.4 molar solution of coupling reactant DIPCD (16 mmol total) in DCM was then added. The AAs were coupled one hour with shaking. The combined bags were washed with 1×100 ml DMF and 1×100 ml DCM, and the His DNP-blocking group was removed with 99 ml DMF+1 ml thiophenol; this procedure was repeated. The bags were washed sequentially with 100 ml DMF, 100 ml isopropyl alcohol, and 100 ml DCM, six times.

The bags were placed with 0.5% anisole into separate tubes of a multiple HF apparatus and 5 ml HF was condensed in each tube. The tubes were kept at 0° C. for one hour, the HF was removed with nitrogen gas, and the peptide-resins were dried in a desiccator overnight. The individual bags were washed with 2×5 ml ether to remove anisol, dried, and extracted with 2×5 ml of 15% acetic acid. The extracted dipeptides were lyophilized. A portion of each resin (about 2 mg) was hydrolyzed in gas-phase HCl at 108° for 24 hr and he amino acid composition of each dipeptide mix was determined by the Pico-tag method.

Table 2 given in FIG. 1 shows the results of amino acid (AA) analysis (AAA) of these bags. The AA bound to resin in the bags are shown across the top. The columns show the amounts in nmole of activated AA attached. The amount of coupling (activated) amino acids was in excess, so the amount of each attached to the resin reflects the relative rate constants. Several determinations gave reproducible results.

FIG. 2 shows the data of Table 2 normalized to Phe as an activated AA by dividing the amino acid composition of each dipeptide resin by the amount of Phe coupled to that resin; this then shows the relative reactivities of 18 activated amino acids for 20 amino acid resins. The data are plotted with the fastest reacting activated AA to the left (i.e., Gly). If each amino acid has the same collection of relative rates of attachment to all resins, the heights of the columns within each of the 16 clusters (Asn+Asp and Glu+Gln are single clusters) would be constant. (The cluster for Phe is of course flat, as it is used as a base for normalization.) The results show that, in fact, within a cluster, the heights generally vary no more than about 20%.

The relative heights of the different clusters reflect the relative reactivities of-the various activated amino acids. The average of each cluster thus gives a good (inverse) approximation of the amount of activated AA to be used in coupling mixture AAs to all AA-resins.

Results of the foregoing amino acid analysis are subject to the following reservations: First, Trp and Cys are destroyed in the analysis and thus do not appear with values in the results; these could be further analyzed if necessary. Second, the amides in Gln and Asn are hydrolyzed in the analysis so that the values presented for Glu and Asp represent Glu+Gln and Asp+Ash, respectively. Third, since the amino acid attached to the resin is present in such large amount—i.e., 50% of the total—the small amount of the same amino acid coupled to it cannot be assessed in a particular experiment; however, the approximate amount can be surmised from the other data points.

Example 2

Synthesis of Dipeptide Mixtures

The use of the determined rate constants in preparing dipeptide mixtures is illustrated here. Five different AA-resins were reacted with a mixture of 4 activated AAs. The concentrations of the activated AAs were adjusted using rate constants from Example 1 to give near equimolar products. The synthesis was performed by the T-bag method of Example i and automated synthesizer.

Five 74 micron 1×2 inch polypropylene bags were prepared. The bags were labeled for identity with black india ink, and filled with ¯100 mg of p-methyl-BHA-resin hydrochloride (~0.75 mmol/g, 150–200 mesh). They were combined in a Nalgene bottle (125 ml) and washed 2×25 ml DCM. (All washing and coupling procedures were performed on a mechanical shaker.) The resin was neutralized in the same bottle with 3×25 ml of 5% DIEA in DCM (2 min each) and then washed with 2×25 ml of DCM. The resins were reacted in separate vessels (30 ml Nalgene bottle) with 0.8 mmol (¯10-fold excess) of one of the following amino acids (tBOC-Glu, tBOC-Ile, tBOC-Met, tBOC-Ala, tBOC-Gly) dissolved in 2 ml DCM, using 0.8 mmol (2 ml of a 0.4M solution) of DIPCDI in DCM as a coupling reagent. The coupling time was one hour at room temperature. The bags were combined in a 125 ml Nalgene bottle and washed with 25 ml DMF and then 25 ml DCM. For the coupling the ABI 430/A synthesizer and reagents supplied by the manufacturer were used (except 50% TFA in DCM was used instead of neat TFA), along with a program provided by C. Miles. The five bags containing the different amino acids on the resin (¯0.4–0.5 mmol) were placed into the standard reaction vessel so the resin is towards the bottom. The mixture of activated AA was supplied as a cartridge containing 108 mg (0.467 mmol) tBOC-Leu, 77 mg (0.292 mmol) tBOC-Phe, 198 mg (0.914 mmol) tBOC-Val, 72 mg (0.336 mmol) tBOC-Pro. The total of all amino acids was 2.09 mmol. The ABI Phe program was used for coupling. About 5 mg peptide was removed for peptide resin sequencing and a portion was hydrolyzed for amino acid analysis using conc HCl-propionic acid (1:1) as described by Scotchler, J., *J. Org. Chem.* (1970) 35:3151.

Figure 3:
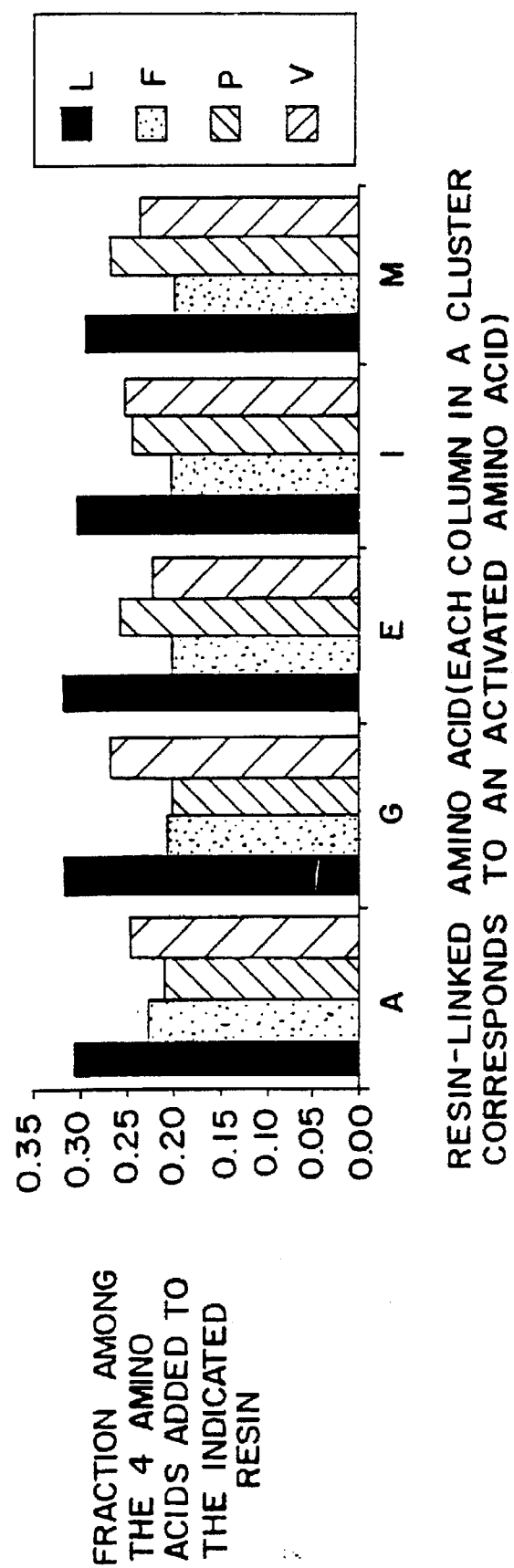
FIG. 3 shows the results of concentration controlled synthesis of amino acid mixtures.

The results are shown in FIG. 3. This shows that the relative rate for each activated AA is quite similar with respect to all resins, and that the resulting mixture is nearly equimolar. A perfect result would give the value 0.25 for each product and equal heights within each cluster. The actual result has a range of 0.20–0.32 and the average is 0.25±0.04 (SD). Overall, each amino acid is no more than 0.8 to 1.28 times the desired amount.

Example 3

Synthesis of Defined Mixtures with Constant Positions

The method of the invention wherein mixtures of amino acid residues alternate with blocks of known constant composition is illustrated in this example. The approach is also applicable to synthesis of mixtures in general.

The peptides $Gly_1$-$AA_2$-$Ala_3$-$AA_4$-$Gly_5$ are synthesized wherein $AA_2$ is selected from Lys, Met, Ser, and Tyr, and $AA_4$ is selected from Leu, Pro, Phe, and Val. The mixture has, therefore, 16 possible peptides. If the rate constants for all possible couplings are known, the product composition can be calculated from the coupling constants and the relative concentrations of the activated amino acids added at each step. Conversely, if the desired product ratio is known, the required concentrations can be derived by a suitable algorithm. Two separate syntheses were conducted, one using equimolar amounts of reactants, and the other using amounts adjusted to form an equimolar mixture of the resulting peptides.

In the first synthesis, conducted on an ABI 430 synthesizer using programs and reagents supplied by the manufacturer, tBOC-Gly-PAM resin was deblocked and coupled to a mixture containing equimolar amounts of the four tBOC amino acids Val, Phe, Leu, and Pro. The resulting bound dipeptides were then coupled to tBOC-Ala, followed by coupling to an equimolar mixture of tBOC-protected Lys, Met, Set and Tyr. Finally, tBOC-Gly was used to provide the fifth residue. The peptide was cleaved from the resin and analyzed to obtain the pertinent rate constant data.

In the second synthesis, the rate constants obtained above were used to calculate the concentration of each amino acid necessary to produce a peptide mixture having equal molar amounts of each peptide product. The synthesis was performed as above, but with the adjusted concentrations.

First Synthesis, Equimolar Reactants

In more detail, 0.62 g (0.5 mmol) tBOC-Gly-PAM resin was obtained in the first cycle. In the second cycle, a mixture (2.0 mmol total) containing 0.5 mmol each of tBOC-Val (0.108 g), tBOC-Phe (0.132 g), tBOC-Leu (0.126 g), and tBOC-Pro (0.107 g) was coupled to the supported Gly using the ABI Phe program. In the third cycle, 0.378 g (2.0 mmol) tBOC-Ala was reacted. In the fourth cycle, a mixture (2.0 mmol total) containing 0.5 mmol each of tBOC-Lys(Cl-Z) (0.207 g), tBOC-Met (0.124 g), tBOC-Ser(OBzl) 0.147 g) and tBOC-Tyr(OBzl) (0.185 g), was coupled using the Lys program. In the fifth cycle, the coupled amino acid was 0.352 g (2.0 mmol) tBOC-Gly.

After each coupling, the resin was analyzed for unreacted free amine and coupling was over 99.7% complete.

The synthesis was interrupted after coupling of the first amino acid mixture and a small sample (ca. 10 mg) was analyzed by sequencing the resin-peptide (ABI User Bulletin No. 4, 1985). The amino acids in [$AA_2$] were not analyzed because of their side-protecting groups. The weight of the peptide-resin at the end of the synthesis was 0.787 g; theoretical is 0.804 g to 0.912 g.

The mixture of peptides was cleaved from the resin using 7 ml condensed HF and 0.7 g p-cresol as scavenger during 1 h at 0°. The HF was removed by a stream of $N_2$ and the excess of p-cresol was removed by extraction with 2×10 ml ethylacetate. The peptides were extracted with 15% acetic acid, lyophilized, dissolved in 5 ml water, and lyophilized again; some material was lost during lyophilization. A white solid was obtained (0.150 g) (theoretical, 0.20g), and was analyzed as described below.

HPLC system: A solution of 100 ul of crude peptide in 10 µl 0.1% TFA/water was loaded on Vydac C18 column (4.6 mm×25 cm). Solvent A was 0.1% TFA in water; solvent B was 0.1% TFA in acrylonitrile (ACN); the standard gradient was 0–55% S in 55 min at a flow rate 1.00 ml per min; the flattened gradient was 0.35% B over 120 min. Detection was at 205–300 nm using a Hewlett-Packard Diode Array Detector (DAD).

Sequencing: For sequencing the pentapeptides attached to resin, 5–10 mg peptide resin was suspended in 100 µl 25% TFA and 5 µl was loaded to ABI 430A gas-phase sequencer using 03RREZ program. For the free peptides, 200 µg of the peptide mixture was dissolved in 1 ml water and 1 µl (400 pm) was loaded to the sequencer (03RPTH program). An on-line PTH analyzer (ABI 120 A HPLC) was used, loading about 25 pm of PTH-AA standards. Quantitation was by computer-assisted integration.

Figure 4A:
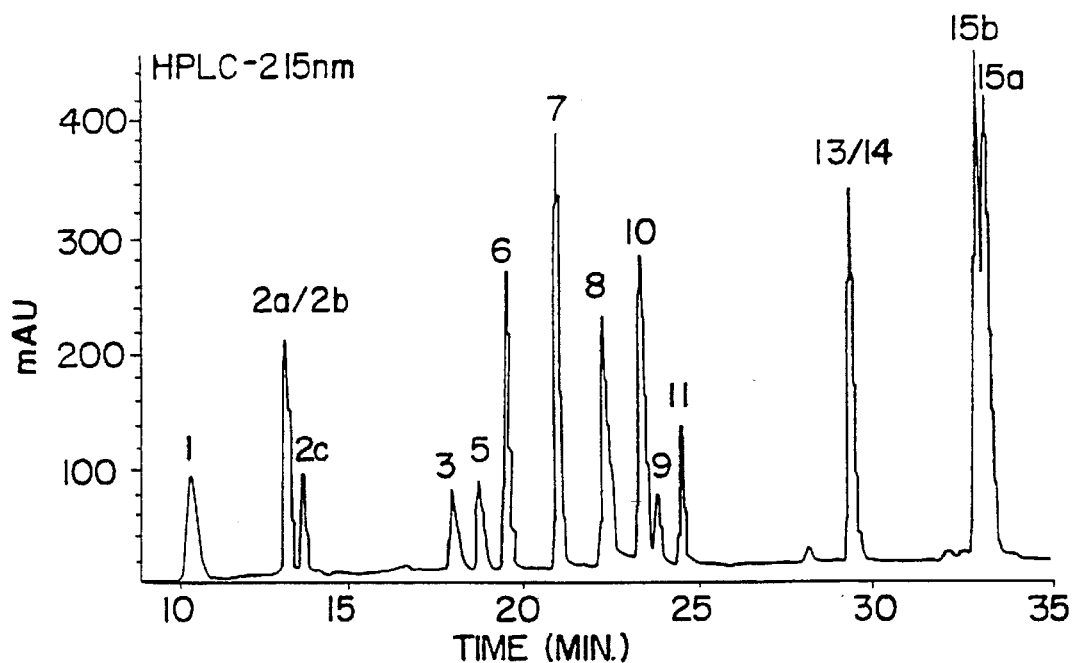
FIGS. 4A and 4B show HPLC traces in one and two dimensions respectively of a peptide mixture.

FIG. 4A shows a single-wavelength HPLC chromatogram of the pentapeptide mixture Gly-[Lys,Met, Ser,Tyr]-Ala-[Leu,Pro,Phe,Val]-Gly from the initial systhesis. In this determination, 15 of the 16 expected peptides were identified; each of these 15 peptides contained the appropriate AAs in the expected stoichiometry. Peak 2a/2b shown in FIG. 4A, contains two sequences: Gly-Ser-Ala-Val-Gly and Gly-Lys-Ala-Leu-Gly. The former is one of the expected peptides, but the latter is identical to the peptide in peak 3. Since 18 is probably a highly hydrophobic peptide (by RV), we suspect it may still contain the Lys-blocking group (Cl-Z). Also, peak 15 contains two peptides, Gly-Phe-Ala-Met-Gly and Gly-Phe-Ala-Tyr-Gly. This conclusion was confirmed by mixture sequencing of the purified peak. These two peptides were later separated on HPLC by lowering the steepness of the gradient to 0–35%B, 120 min.; the peak areas were nearly identical (10700 vs 10794, respectively).

Only one of the expected 16 peptides was not identified in this HPLC analysis. Since all peptides are evident by sequence analysis, we presume this peptide was present but undetected. Two sets of peaks (4 and 13; 9 and 15a) seem to contain the same AAs and thus have the same sequence; the faster moving minor peaks in each set were assigned as the Met-sulfoxide, formed during workup. Peaks 16, 17, and 19 are each missing one of the mixed amino acids (they appear as tetrapeptides) and cannot be assigned from these data.

Figure 4B:
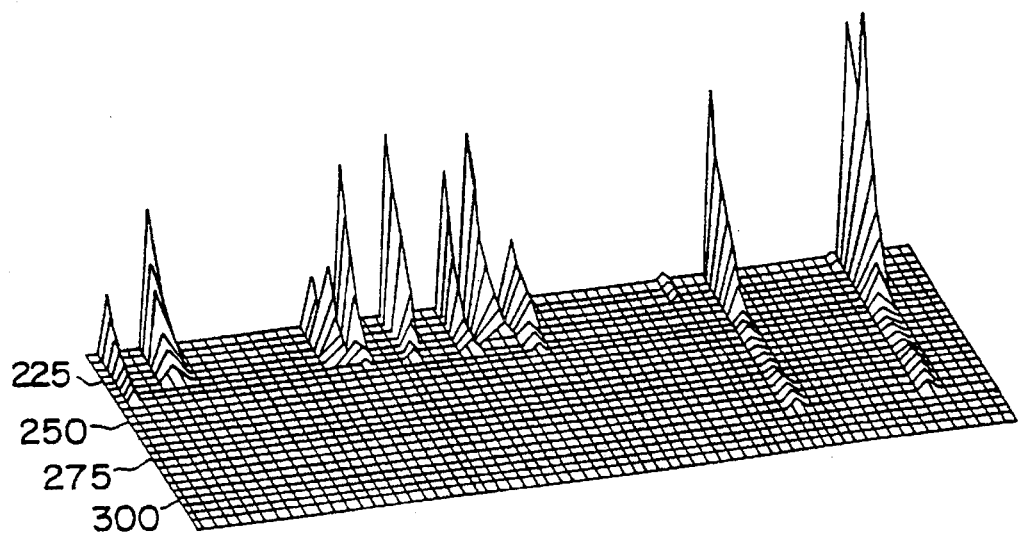

FIG. 4B shows the same mixture using the multi-wavelength detection of a Hewlett-Packard Diode Array Detector (DAD). The results shown in FIG. 4B provide complete spectra for each of the peaks; notably, the aromatic side chains can be seen above 240 nm and peptides containing Trp,Tyr,Phe can be readily identified.

Figure 5:
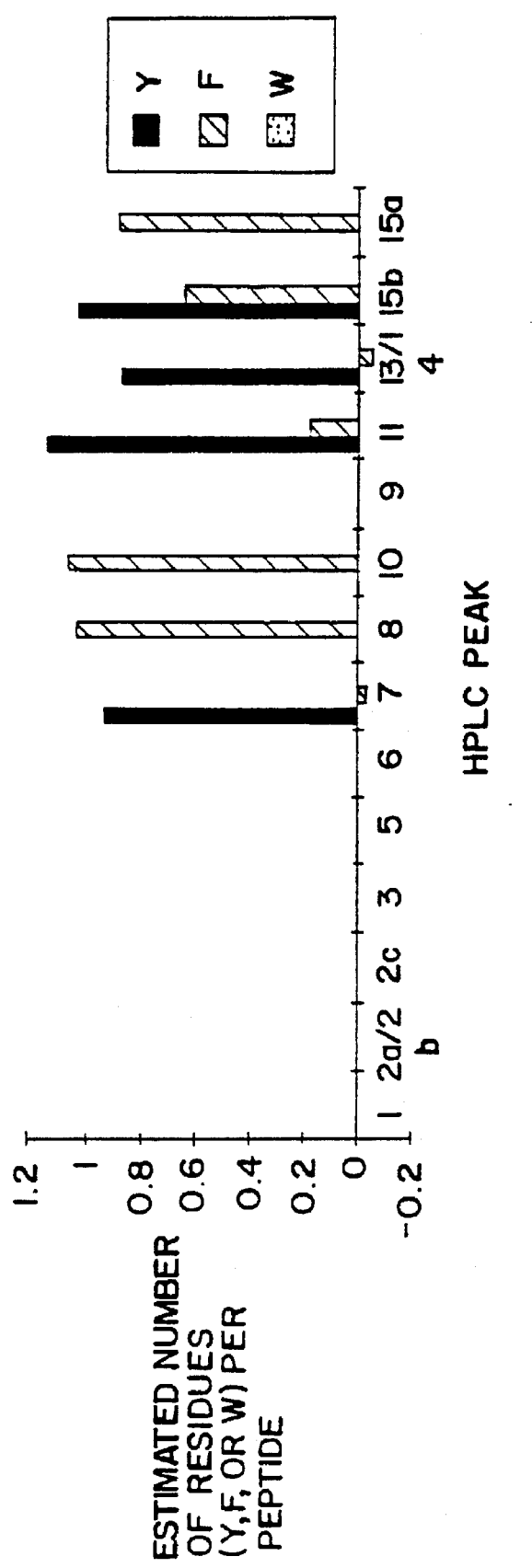
FIG. 5 shows a graph of absorbance areas obtained from HPLC of a pentapeptide mixture.

FIG. 5 shows estimates of the amounts of each aromatic amino acid in each peptide, using ratios of integrated absorbances at 215, 254 and 280 nm and second derivative analysis (which, for example, rules out Trp in these cases). FIG. 5 shows a plot of the HPLC peaks of FIG. 4A vs. number of aromatic AAs (no peptides have Trp; 3 peptides (8, 10, 15a) have 1Phe only; 3 peptides (6, 11, 13) have 1Tyr only; 1 peptide (15b) has 1 Tyr and 1 Phe).

A sample of each peak from a parallel run (not shown) of the same sample was subjected to AAA; in this run peaks 13 and 14 were separated, but 15a and 15b merged into peak 15, and the peaks labeled 2a/2b and 2c in FIG. 4A merged as well into a single broad peak, peak 2. An early fraction, a late fraction, and a pooled fraction of peak 2 were separately analyzed; peak 15 was separated on another HPLC run by reducing the gradient to 0–35%B, 120 min, and the separated peaks were collected for AAA. Table 3, shown in FIG. 6 shows these results.

From these data 15 of the 16 expected peptides were clearly identified. The remaining one of the predicted 16 peptides (Gly-Lys-Ala-Val-Gly) was deduced to be in the pool of peak 2, as evidenced by the mixed AA analysis; it is masked by the two known peptides (Gly-Lys-Ala-Pro-Gly and Gly-Ser-Ala-Val-Gly) in the peak. Each of the 15 peptides identified contains the appropriate AAs in the expected stoichiometry. Two small peaks (4 and 12) seem to contain the same AAs and thus have the same sequence as two of the major peaks (13 and 15a, respectively); the faster moving minor peak in each set was assigned as the Met-sulfoxide, formed during workup.

Table 4 (FIG. 7) gives the results of sequencing the peptide-resin and the HF-cleaved peptide mixture. From sequencing the peptide-resin, the mixture of four AAs in position 2 were not identified because of the blocking group on the AAs. After HF cleavage, which provides the unblocked peptide, each of the AAs in positions 2 and 4 were identified and quantitated. Some loss of free peptide from the filter occurred with each cycle, but the relative amounts of AA in each cycle should be accurate. In both sequencing experiments the intervening Ala cycle was clean (i.e., no other AAs were observed).

Table 4 also gives analyses of the mixture of peptides. The normalized amounts are in good agreement with the values obtained by sequencing. The Val may be slightly underestimated by sequencing of free or resin-bound peptide since the higher AAA value probably provides a more accurate value. The Pro may be overestimated in sequencing of the free peptide, and Tyr may be slightly underestimated (due to part destruction) in AAA.

$AA_4$ defines the mole fractions of each of four sets of peptides and each of these sets contains four peptides defined by the AAs in $AA_2$. Because of the expansion in numbers of peptides at coupling of $AA_2$, the ambiguities do not permit direct quantitation of individual sequences. For the sequence assignment in Table 4 it was assumed that coupling of any AA at $AA_2$ is independent of the variable AA at position 4. In this manner, the amount of each of the peptides (mole fraction $AA_2$×mole fraction $AA_4$=mole fraction peptide) was calculated. Estimating the composition of the pentapeptide mixture using data from sequencing the free peptides, and from AAA (Table 3), the compositions deduced (Table 4) are in fairly good agreement.

Using the composition of the peptides in the mixture produced above, as to the relative amounts of variable AAs, as determined by sequencing the free peptides and the amount of reactants used, the rate constant for each coupling was calculated (Table 4, FIG. 7). The resulting relative rates are in reasonable agreement with those of the Kemp and Kovacs values for coupling to Gly, except for Val, which here reacts faster. This discrepancy is attributed to different methods of coupling, i.e., p-nitrophenyl vs symmetrical anhydride. The conclusion that the rate constant for coupling of Val is indeed different is supported by the results of the reaction of a mixture of these amino acids (and others) with Gly-resin as described elsewhere in the "20×20 experiment" and also shown in this table.

Adjusted Reactants

Based on the rate constants obtained above, a second synthesis was designed and performed using an analogous method. To 0.5 mmol Gly-PAM resin was coupled 0.12 g (0.48 mmol) tBOC-Leu, 0.08 g (0.308 mmol) tBOC-Phe, 0.21 g (0.95 mmol) tBOC-Val, and 0.06 g (0.26 mmol) tBOC-Pro. After coupling 0.39 gm tBOC-Ala (2 mmol), a mixture of four amino acids were coupled: 0.26 g (0.64 mmol) tBOC-Lys(Cl-Z), 0.13 g (0.53 mmol) tBOC-Met, 0.17 g (0.46 mmol) tBOC-Tyr(OBzl), and 0.11 g (0.37 mmol) tBOC-Ser(OBzl). Finally, the N-terminal tBOC-Gly (0.35 g; 2 mmol) was coupled. The mixture was processed as described for the above synthesis, some material was lost during lyophilization. The weight of the mixed peptides was 120 mg.

The reaction amounts were designed to produce peptide mixture with equimolar amounts of each peptide (i.e., 25% of peptide has each candidate amino acid in each mixture position). The synthesis was performed with 99.78% to 99.83% coupling efficiency. Analysis of the peptide mixture was performed, as above, by sequencing free and resin-bound peptide, as well as amino acid analysis. As before, Peak 13 was large and suspected to consist of two peptides. It was rechromatographed using the flattened gradient to resolve two peaks. The AAA of the two peaks were in accord with the structures (Peak 13: Gly-0.71, Ala-0.34, Met-0.32, Phe-0.33; peak 14: Gly-0.55, Ala-0.26, Tyr-0.24, Phe-0.25). With the exception of Pro, which appears low on resin-peptide sequencing, agreement among the methods is excellent. The analysis indicates that the component AAs at each of the two mixture sites are present in nearly the same ratio (0.25±0.05 S.D.), significantly more similar than the first experiment. The average of all analyses was used for these calculations. If the sequencing results of the free peptides are used (the method used to determine the k values), the error is slightly less at 0.25±0.04; the range is 0.2 to 0.31.

It was thought that the low Pro in this experiment might be due to an erroneous relative rate constant derived from sequencing of the free peptide (Table 4, above); as noted, both AAA and sequencing of the peptide resin in the first experiment gave lower Pro values and, if these were used, would have prompted the use of more Pro to achieve equimolar peptides. Several mixed dipeptides ($AA_4$-AA-resin) were thus made using relative rate constants obtained from the peptide-resin sequence quantitation in Table 4; also, the ABI synthesizer was used to couple the mix to 4 AA-resins contained in the reaction vessel. AAA of the peptides showed coupling of a mixture of Leu, Phe, Pro, Val to Gly-resin proceeded as predicted with SD/Mean=0.15. Further, coupling of the mix to resins (Ala, Glu, Ile, and Met) went as expected, with variations SD/Mean ˜0.15. As predicted, the relative rate constant used for Pro in the initial coupling was an erroneous one; a lower value should henceforth be used.

Example 4

Synthesis of Di-, Tri-, Tetra- and Pentapeptides

This examples describes the synthesis of balanced mixtures of the 3,200,000 possible pentapeptides, 160,000 tetrapeptides, 8000 tripeptides, and 400 dipeptides, in a manner similar to the synthesis of mixed peptides described in Examples 1–3 except that the AA-resins are not separated.

An equimolar mixture of the 20 AA-PAM-resins is prepared; the mixture is reacted to completion with a mix of C-20 activated N-blocked amino acids. A portion of the dipeptide mixture is removed and deblocked; the reaction is repeated with an identical mix of amino acids, and the cycle is repeated several times. The amounts of amino acids used are based on relative rate determinations, and adjusted to approximate first-order kinetics by having each amino acid in at least 10-fold excess over its final product. Relative rates are determined by averaging from values given in FIG. 1 and additional data.

The 20 tBoc-AA-PAM resins (ABI) were combined to give an equimolar mixture of 1 mmol of total resin-linked, protected (9 of 20), tBoc-AA. The resin mixture was swollen in 2×50 ml DCM, and filtered. The tBoc protecting group was removed and the resin neutralized as described previously.

A mixture of 20 tBoc-amino acids was prepared by dissolving the following (total of 20 mmol) in 6.0 ml DMF/44 ml DCM:
Gly, 84 mg=480 umol;
Ala, 113 mg=599 umol;
Arg (Tos), 286 mg=666 umol;
Phe, 177 mg=668 umol;
Glu(OBzl), 230 mg=682 umol;
Gln, 168 mg=682 umol;
Met, 176 mg=705 umol;
Pro, 157 mg=730 umol;
Asp(OBzl), 238 mg=737 umol;
Asn, 171 mg=737 umol;
Leu, 185 mg=801 umol;
Ser(Bzl), 243 mg=825 umol;
Lys(Cl-Z), 387 mg=933 umol;
Tyr(Br-Z), 485 mg=981 umol;
Thr(Bzl), 451 mg=1459 umol;
His(DNP), 668 mg=1585 umol;
Val, 510 mg=2349 umol;
Ile, 667 mg=2889 umol;
Cys(4-me-Bzl), 268 mg=825 umol;
Trp, 203 mg=668 umol.

The amino acid mixture was combined with the resin mixture; 30 ml of a 0.67 molar solution of coupling reactant DIPCD (20 mmol total) in DCM was then added and the AAs were coupled one hour with shaking. The resin was washed with 2×80 ml DMF and 2×80 ml DCM. An aliquot (50 umol peptide-resin) was removed, dried, weighed and saved for subsequent treatment with DMF+1 ml thiophenol (DNP-His deblocking) and HF cleavage as before to give the mixture of 400 dipeptides.

This process was repeated on the remaining resin 3 more times, to give the mixed tri-, tetra- and pentapeptides.

Example 5

Selection for Binding to Papain.

N-acetyl phenylalanyl glycinaldehyde is a potent inhibitor of papain; the Phe group binds to the P2 site of papain and the aldehyde binds the active site thiol in a reversible covalent bond. A mixture of various N-acetyl aminoacyl glycinaldehydes was treated with papain and the components capable of binding to papain were selected.

Papain (15 uM) and DTT (10 mM), potassium phosphate (20 mM)-EDTA (1 mM), pH 6.8 (P-E buffer) and a mixture of the N-acteyl aminoacylglycinaldehydes of Phe Gly, Ala, Val, Leu, Ile, Met, Pro, Asn and Gln (25 uM each, 250 uM total inhibitor) were added. Total volume was 300 ul; concentrations given are for the final mixture. After 10 min. at room temp., 150 ul was applied to a Sephadex G-10 column (1 cm×4.2 cm, 3 ml column volume) at 4° C. The column was equilibrated and eluted in P-E buffer at 0.45 ml/min.

The fractions corresponding to the void volume were collected and treated with 14 mM thiosemicarbazide in 0.1M HCl to convert the aldehydes to thiosemicarbazones. The products were analyzed on a Vydac C18 column eluted with an 0 to 60% water/acetonitrile gradient using diode array detection.

The main fraction contained a predominance of the Phe analog derivative (0.7 uM phe/3 uM; initially present as the N-acetyl phenylalanyl glycinaldehyde-papain complex) which is at least 10-fold enriched over the other analogs.

We claim:

1. A method of obtaining a peptide having a desired target property, comprising the steps of:
   providing a mixture of candidate peptides wherein the peptides are attached to a solid support and said mixture comprises 8,000 or more different peptides of distinct, unique and different amino acid sequences, wherein the presence of each peptide in the mixture is predetermined, each peptide is present in the mixture in retrievable and analyzable amounts and the mixture includes at least one biologically active peptide in a retrievable and analyzable amount; and
   selecting from among the mixture of candidate peptides a peptide having a desired target property by exposing the mixture of candidate peptides to a substance to which the peptide having a desired target property will preferentially bind.

2. The method as claimed in claim 1, further comprising:
   isolating the selected candidate peptide having the desired target property.

3. The method as claimed in claim 2, further comprising:
   identifying the isolated candidate peptide having the desired target property.

4. The method as claimed in claim 1, wherein the mixture of candidate peptides contains 160,000 or more different peptides of distinct, unique and different amino acid sequences, each in retrievable and analyzable amounts, and wherein the presence of each peptide in the mixture is predetermined.

5. The method as claimed in claim 1, wherein the mixture of candidate peptides contains 3,200,000 or more different peptides of distinct, unique and different amino acid sequences, each in retrievable and analyzable amounts, and wherein the presence of each peptide in the mixture is predetermined.

6. The method as claimed in claim 1, wherein the mixture of candidate peptides contains 64,000,000 or more different peptides of distinct, unique and different amino acid sequences, each in retrievable and analyzable amounts, and wherein the presence of each peptide in the mixture is predetermined.

7. A method of obtaining a peptide having a desired target property, comprising the steps of:
   providing a mixture of candidate peptides wherein the peptides are attached to a solid support and said mixture comprises 8,000 or more different peptides of distinct, unique and different amino acid sequences, wherein the presence of each peptide in the mixture is predetermined and each peptide is present in an amount such that each peptide is analyzable; and
   selecting from among the mixture of candidate peptides a peptide having a desired target property by exposing the mixture of candidate peptides to a substance to which the peptide having a desired target property will preferentially bind.

8. The method as claimed in claim 7, further comprising:

isolating the selected candidate peptide having the desired target property.

9. The method as claimed in claim 8, further comprising:

identifying the isolated candidate peptide having the desired target property.

10. The method as claimed in claim 7, wherein the mixture of candidate peptides contains 160,000 or more different peptides.

11. The method as claimed in claim 7, wherein the mixture of candidate peptides contains 3,200,000 or more different peptides.

12. The method as claimed in claim 7, wherein the mixture of candidate peptides contains 64,000,000 or more different peptides.

13. A method of obtaining a peptide having a desired target property, comprising:

a) synthesizing a mixture of peptides by reacting a predetermined amount of an activated amino acid residue with the acceptor amino acid or peptide in a manner so as to obtain a mixture of peptides wherein the peptides are attached to a solid support and said mixture comprises 8,000 or more different peptides of distinct, unique and different amino acid sequences wherein the presence of each peptide in the mixture is predetermined, each peptide is present in the mixture in retrievable and analyzable amounts; and b) selecting peptides having one or more desired target properties by exposing the mixture of peptides to a substance to which the peptides having one or more desired target properties will preferentially bind.

14. The method of claim 13 wherein the peptide mixture contains 160,000 or more peptides in known quantities.

15. The method of claim 14 wherein the peptide mixture contains 3,200,000 or more peptides in known quantities.

16. The method of claim 15 wherein the peptide mixture contains 64,000,000 or more peptides in known quantities.

17. A method of obtaining a peptide having a desired target property, comprising:

a) combining and reacting activated amino acids with an acceptor amino acid or peptide, wherein the concentration of each activated amino acid added is varied depending on its coupling constant so as to obtain a candidate mixture of peptides wherein each peptide of the candidate mixture is attached to a solid support and is present in a predicted and analyzable amount;

b) selecting peptides having one or more desired target properties by exposing the candidate mixture to a substance to which the peptide having one or more desired target properties will bind; and c) isolating peptides which selectively bind to the substance.

18. The method of claim 17, wherein selecting step b) is further comprised of a second selection step, such that the resulting selected peptides exhibit a greater degree of the desired target property.

19. A method of obtaining a peptide ligand from a candidate mixture of peptides wherein the peptides are attached to a solid support, said peptide ligand being a ligand of a given target molecule, comprising:

a) combining and reacting activated amino acids with an acceptor amino acid or peptide, wherein the concentration of activated amino acid added is varied depending on its coupling constant, such that each peptide of the candidate mixture is present in a predicted and analyzable amount; and b) isolating peptides having an increased affinity to the target molecule by exposing the candidate mixture to a substance to which peptides having an increased affinity to the target property will preferentially bind.

20. The method of claim 19 wherein the mixture comprises natural coded amino acids.

21. The method of claim 19 wherein the mixture comprises alternate amino acids.

22. The method of claim 19 wherein the mixture comprises D-amino acids.

* * * * *